United States Patent [19]

Brendl et al.

[11] 4,250,389

[45] Feb. 10, 1981

[54] DEVICE FOR IDENTIFYING X-RAY FILMS

[75] Inventors: Rudolf Brendl; Johann Finkenzeller, both of Erlangen; Karl Weiss, Buckenhof, all of Fed. Rep. of Germany

[73] Assignee: Siemens Aktiengesellschaft, Berlin & Munich, Fed. Rep. of Germany

[21] Appl. No.: 946,604

[22] Filed: Sep. 28, 1978

[30] Foreign Application Priority Data

Oct. 24, 1977 [DE] Fed. Rep. of Germany ....... 2747591

[51] Int. Cl.³ ........ H05G 1/28

[52] U.S. Cl. ........ 250/476

[58] Field of Search ........ 250/476

[56] References Cited

U.S. PATENT DOCUMENTS

| | | | |
|---|---|---|---|
| 3,600,577 | 8/1971 | Lovison | 250/476 |
| 3,710,106 | 1/1973 | Loucheur | 250/476 |
| 3,953,738 | 4/1976 | Huttner | 250/476 |

*Primary Examiner*—Craig E. Church

*Attorney, Agent, or Firm*—Hill, Van Santen, Steadman, Chiara & Simpson

[57] ABSTRACT

In an illustrative embodiment, a patient card insertable into the device has the patient data thereon light projected onto the x-ray film with the aid of a light source and an optical image reproducing system; variable data in addition to the data of the patient card are brought into the data field so as to be light-projected onto the x-ray film in a common region and with a common orientation.

1 Claim, 3 Drawing Figures

DEVICE FOR IDENTIFYING X-RAY FILMS

BACKGROUND OF THE INVENTION

The invention relates to an arrangement for the identification of x-ray films with the aid of a patient's data card which can be inserted into the device; a light source and an optical image reproducing system are provided in order to transfer the data onto the x-ray film.

In x-ray examination apparatus, in order to identify x-ray photographs, it is conventional to insert punched-out characterizing letters, most often an L for left and an R for right, into the path of the x-rays and to light-project them during the x-ray exposure. The additional data relating to the patient were often separately light-exposed in the darkroom directly prior to development. Thereby mix-ups could occur, particularly when many x-ray photographs were produced in large clinics. Additional data such as the direction of the radiation relative to the patient were, if at all, plotted later by hand on the developed x-ray photograph with the aid of a pen. This method in which the data were applied to the x-ray sheet film at various times, was not only cumbersome and led to mix-ups again and again, it also led to the result that many details were abandoned.

When using x-ray film cassettes provided with a window, it is known from the German Letters Patent No. 23 27 385 and U.S. Pat. No. 3,962,585 to open the cassette window in a specific arrangement provided therefor. The data of a patient's data card, simultaneously inserted into the arrangement, are light-projected optically in this arrangement onto a field of the x-ray film located therebehind. In order to identify the beam direction, it is possible according to U.S. Pat. No. 3,962,585, to insert the cassette into the light-projection arrangement alongside of two different guides. During the insertion alongside of the one guide, an inverting prism is simultaneously inserted into the beam path so that the lettering is light-projected in mirror-inverted fashion. In this manner, the orientations "ap" (anterior-posterior) and "pa" (posterior-anterior) can be differentiated. However, in this arrangement no possibility exists to light-project additional variable data on the x-ray film. The possibility of mix-ups is also not completely eliminated.

By means of the German Offenlegungsschrift No. 23 46 576 an x-ray examination apparatus with magazine technique is known to light-project the patient's data card directly after the x-ray exposure during the transport of the loose film sheet that was presently exposed. How other constant invariable patient's data, recorded on the patient's card, are to be light-projected is not disclosed in this German Offenlegungsschrift.

SUMMARY OF THE INVENTION

The invention has the underlying objective to indicate a way how not only the constant invariable patient's data, but also additional data, characterizing the exposure conditions, are to be light-projected onto the x-ray film. The operational expense for the handling should thereby be held as small as possible. Mix-ups should definitely be eliminated and the technical expense necessary should be held as small as possible.

In a device of the initially mentioned type, variable data in addition to the desired data of the patient's card can be brought into the data-field to be light-projected. The presupposition is thereby provided to record variable data, such as the date, or a symbol for the direction of the radiation relative to the patient, on the x-ray film.

The readability of the data light-projected on the x-ray film is facilitated when at least one data carrier for the variable data can be inserted above the patient's card and directly alongside of the data field of the patient's card to be light-projected. Thereby it is obtained that the light-projected data are on the x-ray sheet film in one block next to one another and can be read with one glance. Although such a combination of data requires more room on the sheet film, it nevertheless saves time in the evaluation of the x-ray photographs vis-a-vis a resolution in which the light-projected data are distributed in the four corners of the sheet film.

In a particularly advantageous further development of the invention, the variable data can be applied to a band and can be transported with the band into the data field to be light-projected. This resolution facilitates in a very simple fashion bringing those data or symbols and numbers into the data field which are to be light-projected, by means of turning the band.

The handling of the device is notably facilitated if the data carriers for the variable data can be adjusted with a switch lever which can be adjusted alongside of a scale with the data to be selected. This has the great advantage that the data can directly be adjusted on the x-ray examination apparatus by hand during the adjustment of the apparatus. Mix-ups are thereby eliminated. The adjustment can be checked with one glance toward the x-ray examination apparatus. In a multiplicity of cases, specific radiation directions are maintained in many patients so that the corresponding orientation data settings are not altered in that case, but only the patient data.

In an additional expedient inventive embodiment, several data carriers can be provided next to one another which can be adjusted independently from one another. Thereby the information content of the light-projectable data can be significantly increased.

Additional details of the invention are more closely explained in a sample embodiment with the aid of the accompanying sheet of drawings; and other objects, features and advantages will be apparent from this detailed disclosure and from the appended claims.

DETAILED DESCRIPTION

Figure 1:
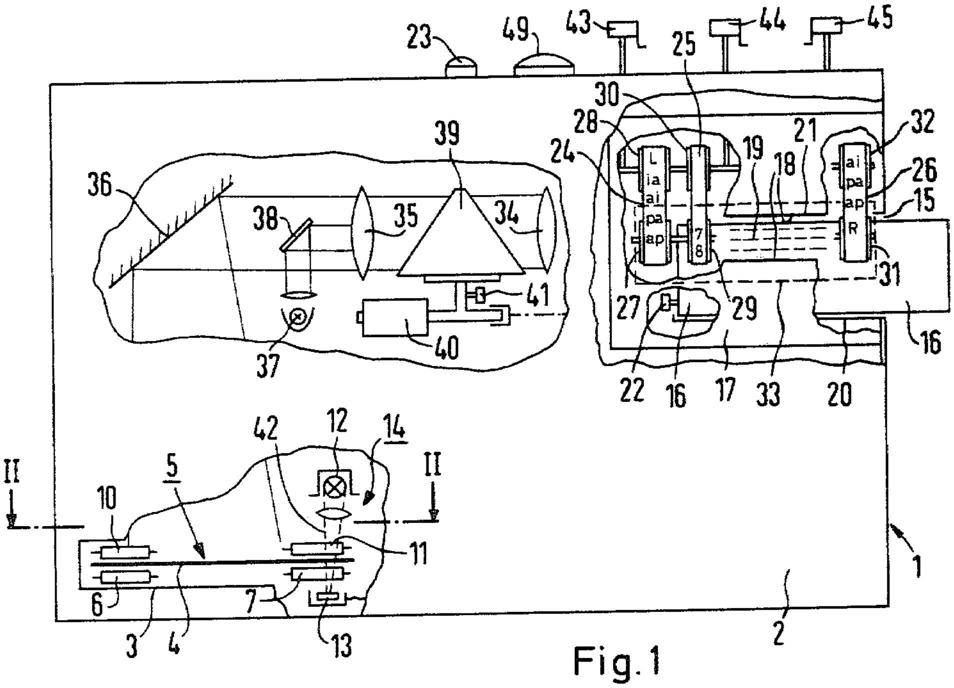
FIG. 1 illustrates a diagrammatic view of the partially broken-open device for the identification of x-ray films.

The device 1 for the identification of x-ray films, shown in FIG. 1, is designed for building into x-ray examination apparatus. The housing 2 of the device is provided with two slots 3 (only one visible) at the front and rear sides thereof providing for the passage through the housing of exposed x-ray film sheets 4. The housing 2 of device 1 is therefore to be built into an x-ray examination apparatus (not illustrated here) such that the input front slot 3 and output rear slot are located in the transport path for the exposed film sheets of the x-ray examination apparatus. The transport path 5 for the film sheets thus becomes a component of the total transport path for the x-ray film sheets in the x-ray examination apparatus. The transport path 5 for the x-ray film sheets in the inventive device 1 is provided with transport rollers such as rollers 6, 7, 8, 9, 10, 11 shown in FIGS. 1 and 2, the rollers being on both sides (e.g. above and below the transport path 5) in order to convey the x-ray film sheets 4. A light barrier 14 consisting of a red light source 12 and a beam detector 13 is installed between the transport rollers (as indicated at 13 in FIG. 2) with a vertically oriented light path in relation to the transport plane (as indicated at 42 in FIG. 1) for the scanning of the edge of the film sheets 4 transported through the transport path. For example, the light barrier system may be actuated by the transition produced as the trailing edge of a film sheet 4 moves past detector 13, FIG. 2.

The housing 2 of device 1 is provided with a third insert slot 15 for sliding-in the patient card 16. In the area of this insert slot, the housing 2 of the device for the identification of the x-ray films is shown broken-open. Behind the broken-open wall of housing 2, one recognizes a cover mask 17 having a slot 18 for the data field 19 to be light-projected, and behind the cover mask guides 20, 21 for the patient card 16 to be inserted, can be recognized. At the end of the insert path for patient card 16, a limit switch 22 operable by the completely inserted patient card, is built in. This limit switch is connected to a signal lamp 23. As can be recognized from FIG. 1, three different transport bands 24, 25, 26 are built in behind the cover mask 17, however still above the plane of patient card 16. The transport bands are mounted respectively on pairs of transport rollers 27, 28; 29, 30; and 31, 32. The transport bands 24, 25, 26 are arranged such that respectively one transport roller of each of these transport bands is respectively situated either to the right or to the left of the field provided for the light-protection of the constant patient data of patient card 16. This field is determined by the slot 18 in the cover mask 17. The slot 18 simultaneously exposes that segment of each of the transport bands selected for light-projection onto the x-ray film sheet position determined by light barrier system 14.

in the illustration of FIG. 1, above the field exposed for light-projection through the cover mask 17, a mirror 33 is situated, tilted by an angle of 45° vis-a-vis the plane of FIG. 1. Said mirror is partially indicated by dashes in FIG. 1. The data on the transport band 24, 25, 26 and of the patient card 16, not covered by the cover mask 17, are light-projected by means of the tilted mirror 33, two lenses 34, 35 and an additional mirror 36 onto the film sheets transported alongside of the transport path 5 for the film sheets. For the correct light-projection, a flash lamp 37 is built in. The flash lamp is controlled by the light barrier 14 to produce a flash of light when each film sheet 4 reaches a correct position for projection of the data field 19 thereon. Said lamp projects its light onto the data field 19 to be light-projected, via a semi-transparent mirror 38. In order to avoid the use of semi-transparent mirror 38, deviating from the illustration of FIG. 1 it is also possible to project the light of the flash lamp directly onto the data field 19 to be light-projected via a separate optical path. An inverting prism 39 is shown in the beam path between the two lenses 34, 35 of the image reproducing system. The inverting prism can be pivoted into the beam path via an electric drive 40. The inverting prism 39, when completely pivoted into the beam path, operates a limit switch 41 scanning the position of said inverting prism.

Figure 2:
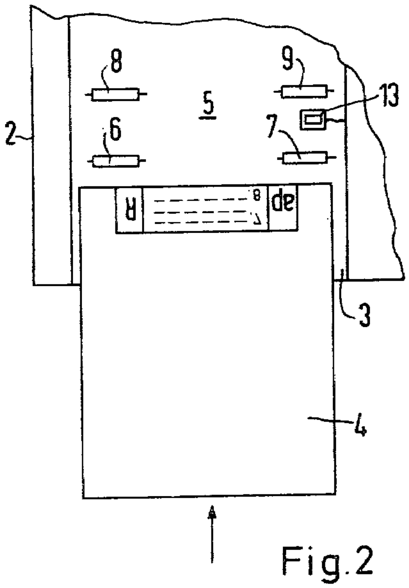
FIG. 2 shows a diagrammatic sectional view taken in a plane parallel to line II—II of FIG. 1.

FIG. 2 illustrates the position of beam detector 13 of the light barrier 14 in the transport path 5 of device 1. The red light beam 42, FIG. 1, crosses the path of the x-ray film sheets 4 at one side of the transport path. On the x-ray film sheet 4, drawn into the transport path 5, the light-projected patient data can be recognized. The complete field 19 of FIG. 1 is, for diagrammatic purposes, shown as it would be projected onto the leading end of film sheet 4 in FIG. 2, in a common region and with the correct orientation so that the entire block of data, after development, will have a common orientation corresponding to that desired for the reading of the x-ray picture associated therewith. It is possible to light-project the patient data on the leading end of the film sheets as diagrammatically indicated in FIG. 2. For the illustrated arrangement, such projection onto the leading end of the film sheet 4 would occur when the signal from the red light beam 42 is utilized during the inlet of the film sheets, and in this case the field 19 may be projected into the region between rollers 6, 7 and 8, 9, for example. When the trailing edge of the film sheets is to actuate the light barrier system 14, during feed of the film sheets out of housing 2, the field 19 may be projected onto a region beyond rollers 8, 9, such that the field is projected onto the trailing end of the film sheet (rather than the leading end as illustrated in FIG. 2).

Figure 3:
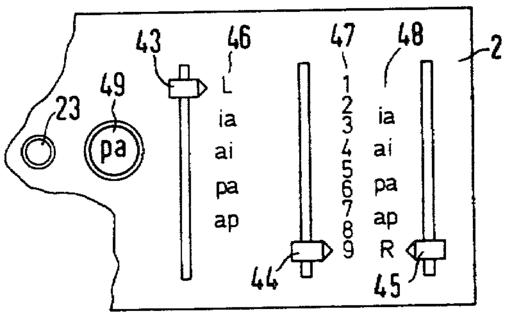
FIG. 3 shows a partial top view of the housing of the device showing the switch levers and the scales assigned thereto for the variable data.

FIG. 3 shows a top view looking toward the housing 2 of the inventive device 1 for the identification of x-ray photographs and showing switch levers 43, 44, 45 for the adjustment of transport bands 24, 25, 26. The switch levers can be adjusted alongside of a respective scale 46, 47, 48. The variable data, visible in the slot 18 of cover mask 17, are given on these scales during the respective position of the switch levers. Additionally, a green signal lamp 23 is built in on the housing 2 of the device for the identification of x-ray films. Said lamp is connected to the limit switch 22 which is built into the insert slot for the patient card. Finally, a signal lamp 49 bearing the letters "pa", can be recognized on the housing of the patient card. Said signal lamp 49 is connected to the limit switch 41 with the aid of which the position of the inverting prism 39 is scanned.

If an x-ray photograph is to be made with the x-ray examination apparatus in which the device 1 was built in in order to identify x-ray films, a patient card 16 of the patient to be examined must firstly be inserted into the insert slot 15 of housing 2 of device 1. The limit switch 22 is actuated by the patient card after the patient card is completely inserted when the data of the patient card to be light-projected are located in the light-projectable field 19 of the device for identifying x-ray photographs. Said limit switch 22 switches on the green signal lamp 23 at the housing 2 of device 1. This signal lamp signals that the device 1 for identifying x-ray photographs is ready for operation. An electric barrier for the release of x-ray photographs can simultaneously be lifted by this limit switch 22. By choosing the radiation direction or the beam path with the aid of which the x-ray photograph is to be made, the radiologist can determine where on the x-ray film sheet 4 either right or left is located by means of adjusting one of the two exterior switch levers 43, 45, and he can reference the radiation directions represented by the notations "ia", "ai", "pa", "ap" with the aid of the other exterior switch lever. He can subsequently set the date of exposure or a corresponding reference number with the aid of the center switch lever 44. When selecting an "ap" projection, the electric drive 40 for the inverting prism 39 is simultaneously switched on via a contact connected to the switch lever, not shown here, and the inverting prism is pivoted into the beam path. Thereby the limit switch 41 is activated by the carrier for the inverting prism. Said limit switch switches on signal lamp 49 on housing 2 of device 1, this signal lamp being referenced "pa" as indicated in FIG. 3. If an x-ray exposure is now released and the exposed film sheet 4 is transported through the transport path 5 of device 1 for identifying x-ray photographs, the signal, released by its rear edge when passing the light barrier 14, is used to release the flash lamp 37. The data field 19 exposed by the slot 18 of cover mask 17, would in this case be light-projected onto the lower edge of the x-ray film sheet (as viewed in FIG. 2) during its transport. By selecting an "ap" exposure, all data are mirror-reflectedly light-projected by means of the inverting prism 39 inserted into the beam path. Thereby the physician, for the evaluation of the x-ray photograph, must view the x-ray picture correctly in order to read the light-projected data on the film sheet.

It is perfectly possible to install a clock with date indicator with the aid of the coupled-on center transport band 25 instead of the center switch lever 44. In that case, the center switch lever 44 could be dispensed with completely.

It will be apparent that many modifications and variations may be effected without departing from the scope of the novel concepts and teachings of the present invention.

I claim as my invention:

1. A device for the indentification of x-ray films with the aid of a patient card insertable into the device, said device comprising:

(a) a housing (2) having a patient card receiving slot (15) for accommodating insertion of a patient card into said housing, and having means (17, 18) defining an elongated single unitary data field region to be occupied centrally by data on an inserted patient card, (b) an optical image reproducing system in said housing including a light source (37) for supplying light to illuminate said data field region, and light directing means (38, 33) in said housing for directing light from said light source (37) to said single unitary data field region for illuminating said data field region for light projection of an image of a single unitary data field occupying said data field region, (c) data carriers (24, 25, 26) at said data field region and each carrying a series of data symbols for selective alignment with said data field region directly alongside of the data on an inserted patient card to form a part of the single unitary data field with the data on an inserted patient card at said data field region, (d) said data carriers each comprising a band having the series of data symbols spaced along the length thereof for selective movement into alignment with said data field region in accordance with the amount of longitudinal movement of the band, and respective ones of said bands being disposed at respective opposite ends of said elongated single unitary data field region so as to provide data symbols aligned with the right and left sides of the data of an inserted patient card, (e) said housing having individually adjustable switch levers (43, 44, 45) accessible at the exterior of the housing, and having respective series of indicia (46, 47, 48) associated with the respective switch levers at the exterior of said housing for indicating the respective ones of said series of data symbols which can be aligned with said data field region, (f) said individually adjustable switch levers (43, 44, 45) being coupled with the respective bands (24, 25, 26) such that positioning of the switch levers at the respective associated indicia of said series causes the corresponding data symbols on the respective bands to be positioned at the respective right and left sides of the data of an inserted patient card, (g) said optical image reproducing system further comprising light image projecting means (34, 35, 36) associated with said data field region for directing a light image of the single unitary data field at said data field region including the data of an inserted patient card and the aligned data symbols to the right and left thereof, and (h) x-ray film positioning means in said housing for positioning an x-ray film in operative association with said light image projecting means (34, 35, 36) so that the light image of the single unitary data field, including the data of an inserted patient card and the data symbols of said bands which are aligned with said single unitary data region, is projected onto an x-ray film positioned by said x-ray film positioning means, in a single work cycle.

* * * * *